United States Patent
Younossi et al.

(10) Patent No.: US 7,824,871 B2
(45) Date of Patent: Nov. 2, 2010

(54) METHODS OF DIAGNOSING NON-ALCOHOLIC STEATOHEPATITIS (NASH)

(75) Inventors: Zobair M. Younossi, Fairfax Station, VA (US); Mohammed H. Jarrar, Reisterstown, MD (US); Vikas Chandhoke, Fairfax, VA (US); Ancha V. Baranova, Annandale, VA (US)

(73) Assignees: George Mason Intellectual Properties, Fairfax, VA (US); INOVA Health System, Falls Church, VA (US)

( * ) Notice: Subject to any disclaimer, the term of this patent is extended or adjusted under 35 U.S.C. 154(b) by 320 days.

(21) Appl. No.: 12/139,173

(22) Filed: Jun. 13, 2008

(65) Prior Publication Data

US 2008/0311593 A1      Dec. 18, 2008

Related U.S. Application Data

(60) Provisional application No. 60/943,914, filed on Jun. 14, 2007, provisional application No. 61/016,164, filed on Dec. 21, 2007.

(51) Int. Cl.
*G01N 33/53* (2006.01)
*G01N 33/543* (2006.01)

(52) U.S. Cl. .................. 435/7.21; 435/7.1; 436/501; 436/518; 422/50; 422/60; 424/9.1

(58) Field of Classification Search .............. None
See application file for complete search history.

(56) References Cited

U.S. PATENT DOCUMENTS 7,314,720 B2    1/2008  Paz et al.

| | | |
|---|---|---|
| 2003/0190802 A1 | 10/2003 | Pressman et al. |
| 2005/0032218 A1 | 2/2005 | Gerlach |
| 2006/0073097 A1 | 4/2006 | Ma et al. |
| 2007/0025883 A1 | 2/2007 | Tai et al. |
| 2007/0072181 A1 | 3/2007 | Blatt |
| 2007/0231811 A1 | 10/2007 | Paz et al. |

FOREIGN PATENT DOCUMENTS

WO   WO 2007/130636 A2   11/2007
WO   WO 2008/021192 A2   2/2008

OTHER PUBLICATIONS

Editorial "The Future is Around the Corner: Noninvasive Diagnosis of Progressive Nonalcoholic Steatohepatitis" Hepatology, vol. 47, No. 2, pp. 1-3 (2008).
Adams et al. "Treatment of Non-Alcoholic Fatty Liver Disease" Postgrad Med J 2006, 82, pp. 315-322.
Younossi et al. A Novel Diagnostic Biomarker Panel for Obestiy-Related Nonalcoholic Steatohepatitis (NASH), Obes. Surg. E-published May 24, 2008.
Notification of Transmittal dated Sep. 12, 2008, from PCT Application No. PCT/US08/07385.
International Search Report dated Sep. 12, 2008, from PCT Application No. PCT/US08/07385.
Written Opinion of International Searching Authority dated Sep. 12, 2008, from PCT Application No. PCT/US08/07385.
International Preliminary Report on Patentability, with Notification and Written Opinion, dated Dec. 17, 2009, in corresponding International Application PCT/US2008/007385.

*Primary Examiner*—Lisa V Cook
(74) *Attorney, Agent, or Firm*—Kilyk & Bowersox, P.L.L.C.

(57) ABSTRACT

Non-invasive methods for detecting non-alcoholic fatty liver disease (NAFLD) and identifying the presence or absence of non-alcoholic steatohepatitis (NASH) in a subject utilize one or more biomarkers. The methods can differentiate between subjects with NASH and those with simple steatosis. Kits containing one or more agents for measuring the level of the biomarkers can be utilized to perform the described methods.

28 Claims, 1 Drawing Sheet

METHODS OF DIAGNOSING NON-ALCOHOLIC STEATOHEPATITIS (NASH)

CROSS-REFERENCE TO RELATED APPLICATIONS

This application claims the benefit under 35 U.S.C. §119 (e) of prior U.S. Provisional Patent Application No. 60/943,914 filed Jun. 14, 2007, and U.S. Provisional Patent Application No. 61/016,164, filed Dec. 21, 2007, and both of which are incorporated in their entireties by reference herein.

FIELD

The present teachings relate to methods for detecting non-alcoholic fatty liver disease (NAFLD) in a subject. More specifically, the present teachings relate to detecting non-alcoholic steatohepatitis (NASH) and to monitoring a subject's response to a therapy.

BACKGROUND

As the clinical importance of non-alcoholic fatty liver disease (NAFLD) is increasingly appreciated, research is focusing on distinguishing its subtypes and staging the extent of hepatic fibrosis. At one end of the NAFLD spectrum is simple steatosis (SS), and at the other end are non-alcoholic steatohepatitis (NASH), and NASH-related cirrhosis and fibrosis. The distinction between NASH and simple steatosis is important because of differences in their potential for progression. Generally, simple steatosis is relatively benign, but NASH can progress to cirrhosis and fibrosis.

NAFLD is generally asymptomatic until severe liver impairment occurs. The costs associated with managing patients with NASH can be substantial, emphasizing the importance of early diagnosis of NASH. If recognized, treatment methods for NAFLD and NASH can slow or reverse the disease in some individuals, particularly in early stage disease.

There are no laboratory tests for NAFLD or NASH. Serum aminotransferase elevations and hepatic imaging studies showing changes suggestive of fatty liver are not adequate alone or in combination to distinguish NAFLD from NASH. At present, liver biopsy with strict pathologic criteria is the only method to accurately establish the diagnosis of NASH or to stage the extent of fibrosis. Despite important technological improvements (for example, automatic biopsy guns, ultrasound guidance), liver biopsy remains costly and is associated with potentially important complications that occur in approximately 0.5% of cases. Additionally, histologic lesions of NASH may not be evenly distributed throughout the liver parenchyma, leading to sampling errors. An inadequate length or fragmented biopsy specimen can make the correct diagnosis even more challenging.

Alternatives to liver biopsy include non-invasive radiological modalities such as ultrasound, computerized tomography, and magnetic resonance imaging. Unfortunately, most of these modalities can only detect hepatic steatosis and are unable to distinguish NASH from simple steatosis or accurately detect hepatic fibrosis. There remains a need for non-invasive methods of detecting and screening for NAFLD and NASH. What is needed are better methods for diagnosing NAFLD and NASH, monitoring disease progression, and determining efficacy of treatment. Additionally, what is needed are better testing methods that can be used to classify and differentiate between subjects with NAFLD and NASH, and to identify subjects at risk of transitioning from NAFLD to NASH.

SUMMARY

The present teachings relate to a method for detecting non-alcoholic fatty liver disease (NAFLD) in a subject by measuring the level of one or more biomarkers in a sample derived from the subject, wherein the one or more biomarkers comprises an adipocytokine, an apoptosis marker, and/or a cell death marker, and analyzing the level in conjunction with a respective reference value range for the one or more biomarkers. The presence or severity of NAFLD in the subject can be diagnosed based on the analysis of the one or more biomarkers. The methods of the teachings for detecting NAFLD can be useful in a variety of patient populations including, but not limited to, those with obesity, impaired glucose metabolism, insulin resistance, and elevated Homeostasis Model Assessment (HOMA) scores. A method of the present teachings can be useful, for example, to differentiate NASH from simple steatosis.

The method can comprise comparing the level of the one or more biomarkers with the one or more respective reference value ranges. In some embodiments, the reference value ranges can represent the level of the one or more biomarkers found in one or more samples of one or more subjects without NAFLD (i.e., normal samples). In some embodiments, the reference values can represent the level of the one or more biomarkers found in one or more samples of one or more subjects with NAFLD.

The present teachings further relate to a method of screening a subject to identify the presence or absence of NASH in the subject by measuring the level of a plurality of biomarkers in a sample derived from the subject, wherein the plurality of biomarkers comprises an adipocytokine, an apoptosis marker, and a cell death marker, and analyzing the levels in conjunction with respective reference value ranges for the plurality of biomarkers.

The present teachings further relate to a method for evaluating the effect of an agent for treating NASH in a subject by analyzing the level of each of one or more biomarkers in samples derived from the subject before and after the subject is treated with the agent, in conjunction with respective reference value ranges for the one or more biomarkers wherein the one or more biomarkers comprises an adipocytokine, an apoptosis marker, and/or a cell death marker.

The present teachings further relate to a method for monitoring the efficacy of a therapy for treating NASH in a subject by analyzing the level of each of one or more biomarkers in samples derived from the subject before and after the subject undergoes the therapy, in conjunction with respective reference value ranges for the one or more biomarkers wherein the one or more biomarkers comprises an adipocytokine, an apoptosis marker, and/or a cell death marker. Such a method can further include, if desired, comparing the presence of or severity of NASH in the subject to the presence and severity of NASH in the subject at an earlier time. The methods of the teachings can be used to monitor, for example, the progression or regression of NASH over time in a subject treated with one or more anti-NASH therapies, or to compare, for example, the efficacies of two or more anti-NASH therapies.

The present teachings further relate to a method of differentiating NASH from simple steatosis in a subject. The method comprises measuring the levels of cytokeratin CK-18 (M65 antigen), caspase-cleaved CK-18 (M30 antigen), resistin, and adiponectin in a subject. The method can further comprise determining the level of a necrosis marker by determining the difference of the measured level of cytokeratin CK-18 (M65 antigen) and the measured level of caspase-cleaved cytokeratin CK-18 (M30 antigen) (i.e., M65–M30).

The methods of the present teachings can be practiced by measuring the level of biomarkers adipocytokine, an apoptosis marker, and/or a cell death marker, without measuring additional biomarkers, or the methods can be combined with a detection method for one or more additional biomarkers, including, but not limited to, visfatin, glucose, insulin, tumor necrosis factor-alpha (TNF-α), interleukin 6 (IL-6), or interleukin 8 (IL-8). The methods of the present teachings can also be practiced in combination with additional diagnostic methods, including, but not limited to, glucose metabolism, insulin resistance, and HOMA score.

The present teachings further relate to a kit comprising a package containing one or more agents for measuring the level of an analyte of interest, wherein the analyte of interest comprises cytokeratin CK-18 (M65 antigen), caspase-cleaved CK-18 (M30-antigen), resistin, or adiponectin, or any combination thereof.

Features and advantages of the present teachings will become apparent from the following description. This description, which includes drawings and examples of specific embodiments, provide a broad representation of the present teachings. Various changes and modifications to the teachings will become apparent to those skilled in the art from this description and by practice of the teachings. The teachings are not intended to be limited to the particular forms disclosed and cover all modifications, equivalents, and alternatives.

BRIEF DESCRIPTION OF THE DRAWINGS

The accompanying drawing, which is incorporated into and constitute a part of the specification, illustrate specific embodiments of the teachings, and taken in conjunction with the detailed description of the specific embodiments, serves to explain the principles of the teachings.

DETAILED DESCRIPTION

Figure 1:
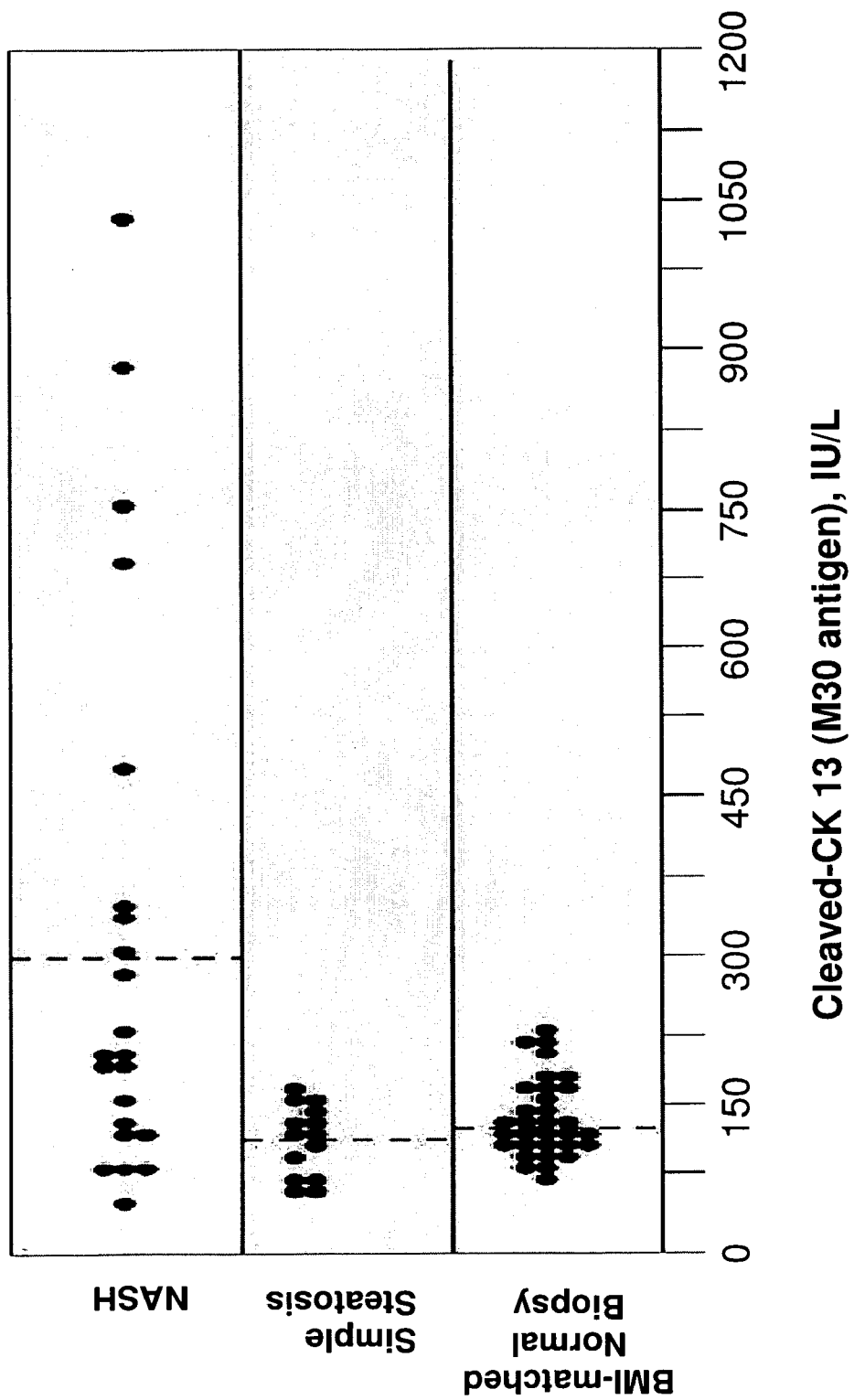
FIG. 1 shows the results of ELISA analysis of caspase-cleaved CK-18 (M30 antigen) in serum samples derived from NASH patients, simple steatosis patients, and normal control patients.

Referring to the drawing and the following detailed description, information about the teachings is provided including the description of specific embodiments. The detailed description serves to explain the principles of the teachings.

As disclosed herein, the serum levels of a number of biomarkers were analyzed in a population of patients undergoing bariatric surgery. Clinical data were obtained at the time of surgery, and a liver biopsy was performed. The patient population included subjects with NASH, simple steatosis, and matched controls (i.e., morbid obesity). A panel of one or more biomarkers performed well in detecting NAFLD in subjects. See Tables 1-3.

Based on these findings, the present teachings provide a method for detecting NAFLD in a subject. The method can be used, for example, for detecting NAFLD in a subject in which NAFLD had not previously been detected, for determining the state or severity of NAFLD in a subject, for monitoring the efficacy of a therapy for treating NAFLD in a subject, and/or for evaluating the efficacy of an agent administered to a subject who suffers from NAFLD. The method can be used, for example, to detect simple steatosis (SS), steatosis with non-specific inflammation, NASH, or NASH-related cirrhosis in a subject, and/or to distinguish NASH from SS in a subject.

According to various embodiments, the method can be used for screening a subject to identify risk factors for NAFLD and/or to detect hidden disease in asymptomatic subjects. Identification of risk factors can allow early intervention to prevent NAFLD progression, and early detection of occult disease can reduce disease morbidity and mortality through early treatment.

According to various embodiments, the method can be used to help diagnose NAFLD. The method can help establish or exclude the presence of NAFLD in symptomatic subjects. The method can assist in early NAFLD diagnosis after onset of symptoms and signs, assist in differential diagnosis of various possible NAFLD diseases, and/or help determine the stage or activity of NAFLD.

According to various embodiments, the method can be used in patient management. For example, the method can help to evaluate the severity of NAFLD, estimate prognosis, monitor the course of NAFLD (i.e., progression, stability, or resolution), detect NAFLD recurrence, select drugs and adjust dosages, and/or select and adjust therapy.

According to various embodiments, a method for detecting NAFLD in a subject can comprise measuring the level of one or more biomarkers in a sample derived from the subject. The one or more biomarkers can comprise, for example, an adipocytokine, an apoptosis marker, a cell death marker, or any combination thereof. The method can further comprise analyzing the level of the one or more biomarkers, in conjunction with a respective reference value range for the one or more biomarkers. The level of the one or more biomarkers can be analyzed by multivariate analysis, for example, by linear regression analysis.

The term "subject" as used herein refers to human beings and animals, for example, mammals. In one or more embodiments, the subjects are human beings of any race, gender, or age.

The terms "non-alcoholic fatty liver disease" or "NAFLD", "non-alcoholic steatohepatitis" or "NASH", and "Simple Steatosis" are each used in the sense which are currently admitted by the scientific community. In general, NAFLD exists as a histological spectrum of changes. All of the stages of NAFLD have in common the accumulation of fat in the liver cells (steatosis). Simple steatosis refers to the hepatic steatosis in the absence of significant inflammation and hepatocellular damage, whereas NASH demonstrates inflammation and hepatocellular damage and sometimes fibrosis.

The term "adipocytokine" or "adipokine" as used herein refers to a group of cytokines secreted by adipose tissue, but also to a group of molecules sometimes referred to as "adipose-derived hormones". Examples of adipocytokines include adiponectin, chemerin, interleukin-6 (IL-6), interleukin-8 (IL-8), leptin, plasminogen activator inhibitor-1 (PAI-1), retinol binding protein 4 (RBP-4), tumor necrosis factor-alpha (TNFα), resistin, and visfatin.

The term "apoptosis" as used herein refers to a form of programmed cell death and involves a series of biochemical events that lead to a characteristic cell morphology, such as cytoplasmic condensation, blebbing of the plasma membrane, condensed chromatin, and DNA fragmentation. Apoptosis is an active process requiring metabolic activity and protein synthesis by the dying cell. Apoptosis stands in contrast to "necrosis", which is a form of traumatic cell death that results from acute cellular injury.

The term "necrosis" as used herein refers to the sum of the morphological changes indicative of cell death and caused by the progressive degradative action of enzymes. Necrosis is associated with rapid metabolic collapse that leads to cell swelling, loss of plasma membrane integrity, and ultimate cell rupture.

The term "apoptosis marker" as used herein refers to a variety of compounds whose presence or absence is considered to be an indicator of apoptosis. Known apoptosis markers include, but are not limited to, annexin V, apolipoprotein C-1, caspase-1, caspase-3, cleaved cytokeratin CK-18 (M30 antigen), cleaved poly ADP ribose polymerase (PARP), tissue polypeptide antigen (TPA), and ubiquitin.

The term "cell death marker" as used herein refers to a variety of compounds whose presence or absence is considered to be an indicator of cell death. Known cell death markers include, but are not limited to, beta-glucoronidase, BV2, cytochrome CK-18 (M65 antigen), isocitrate dehydrogenase (ICDH), serum immunoreactive prolyl 4-hydroxylase (S-IRPH), tenascin-C, and tropinin.

According to various embodiments, the one or more biomarkers can comprise, for example, cytokeratin CK-18 (M65-antigen), caspase-cleaved CK-18 (M30-antigen), resistin, adiponectin, insulin, tumor necrosis factor-alpha (TNF-α), interleukin 6 (IL-6), or interleukin 8 (IL-8), or any combination thereof. In some embodiments, the method can comprise measuring the level of at least 1, at least 2, at least 3, at least 4, at least 5, or at least 10 biomarkers. In some embodiments, the one or more biomarkers can comprise cytokeratin CK-18 (M65-antigen), caspase-cleaved CK-18 (M30-antigen), resistin, and adiponectin. In some embodiments, the one or more biomarkers can comprise cytokeratin CK-18 (M65-antigen), TNF-α, resistin and adiponectin.

According to various embodiments, measuring the level of the one or more biomarkers can comprise reacting with a specific antibody against the one or more biomarkers, or against any fragment of biomarker containing an antigenic determinant. The antibody can comprise, for example, a whole immunoglobulin molecule, a monoclonal antibody, a polyclonal antibody, a chimeric antibody, a recombinant fragment of antibody, an Fab fragment, an Fab' fragment, an F(ab')2 fragment, an Fv fragment, an scFv fragment, or any combination thereof.

The phrase "measuring the level" as used herein refers to any quantitative or qualitative assay for determining the presence of a biomarker, and includes any direct or indirect quantitative assay. A variety of immunoassay formats, including competitive and non-competitive immunoassay formats, antigen capture assays, and two-antibody sandwich assays are useful assay methods. According to various embodiments, measuring the level of the one or more biomarkers can comprise conducting, for example, enzyme-linked immunosorbent assay (ELISA), radioimmunoassay (RIA), immunofluorescent assay (IFA), chemiluminescent assay, sandwich assay, capillary electrophoresis based immunoassay (CEIA), magnetic capture, microsphere capture, and/or western blotting. In some embodiments, measuring the level of the one or more biomarkers can comprise conducting, for example, surface enhanced Raman spectroscopy (SERS), flow cytometry, and/or mass spectrometry. The level of one or more biomarkers can be measured, for example, utilizing the Bio-Plex system (Bio-Rad Laboratories, Hercules, Calif.).

According to various embodiments, the method can comprise measuring the level of one or more biomarkers in a sample derived from a subject and analyzing the level in conjunction with a respective reference value range for the one or more biomarkers. The reference value ranges of each of the one or more biomarkers can represent, for example, a subject without NAFLD. The analysis can comprise multivariate analysis, for example, linear regression analysis, of the level of one or more biomarkers. The analysis can calculate, for example, an optimal threshold for detecting NAFLD. The threshold can be calculated, for example, at a value greater than or equal to about 0.20, a value in a range of from about 0.20 to about 0.70, from about 0.25 to about 0.55, or from about 0.27 to about 0.40. According to various embodiments, a threshold value can be selected to provide a sensitivity for detecting NAFLD in a range of, for example, from about 50% to about 100%, and a specificity for detecting NAFLD in a range of, for example, from about 25% to about 90%.

According to various embodiments, the method can comprise individually measuring the level of one or more biomarkers, each biomarker measured separately, or can comprise measuring the level of one or more biomarkers in a multiplex assay.

According to various embodiments, the sample can be obtained from the subject. The sample can be derived from the subject and can comprise, for example, whole blood, serum, plasma, urine, saliva, tissue, or tissue extract. In some embodiments, samples can be diluted, if desired, prior to analysis. In some embodiments, a single sample can be obtained for the subject and can be subdivided prior to analysis. In some embodiments, two or more samples can be obtained from the subject and the samples can be of the same or a different type.

The clinical parameters of sensitivity, specificity, negative predictive value, positive predictive value and accuracy are calculated using true positives, false positives, true negatives and false negatives. A "true positive" sample is a sample positive for the indicated stage of NAFLD according to clinical biopsy, which is also diagnosed positive according to a method of the teachings. A "false positive" sample is a sample negative for the indicated stage of NAFLD by biopsy, which is diagnosed positive according to a method of the teachings. Similarly, a "false negative" is a sample positive for the indicated stage of NAFLD by biopsy, which is diagnosed negative according to a method of the teachings. A "true negative" is a sample negative for the indicated stage of NAFLD by biopsy, and also negative for fibrosis according to a method of the teachings. See, for example, Motulsky (Ed.), *Intuitive Biostatistics* New York: Oxford University Press (1995).

As used herein, the term "sensitivity" means the probability that a diagnostic method of the teachings gives a positive result when the sample is positive, for example, positive for NASH. Sensitivity is calculated as the number of true positive results divided by the sum of the true positives and false negatives. Sensitivity essentially is a measure of how well a method correctly identifies those subjects with NAFLD. In one or more embodiments, the sensitivity of detecting NASH in a subject can be at least about 70%, and can be, for example, at least 75%, 80%, 85%, 90%, or 95%, in the subject population assayed.

As used herein, the term "specificity" means the probability that a diagnostic method of the teachings gives a negative result when the sample is not positive, for example, not positive for NAFLD. Specificity is calculated as the number of true negative results divided by the sum of the true negatives and false positives. Specificity essentially is a measure of how well a method excludes those subjects who do not have NAFLD. In one or more embodiments, when the sensitivity of detecting NASH in a subject is at least about 95%, the specificity of diagnosing a subject can be in the range of about 70-100%, for example, at least 75%, 80%, 85%, 90% or 95% of the subject population assayed.

The term "negative predictive value," as used herein, is synonymous with "NPV" and means the probability that an individual diagnosed as not having NAFLD actually does not have the disease. Negative predictive value can be calculated as the number of true negatives divided by the sum of the true negatives and false negatives. The term "positive predictive value," as used herein, is synonymous with "PPV" and means the probability that an individual diagnosed as having NAFLD actually has the condition. Positive predictive value can be calculated as the number of true positives divided by the sum of the true positives and false positives.

According to various embodiments, the method can further comprise generating data on the sample indicating the level of one or more biomarkers, and transforming the data into computer-readable form. A computer can be operated to execute an algorithm, wherein the algorithm determines the level of the one or more biomarkers. The level can then be displayed, for example, on a monitor, and/or printed. In some embodiments, an algorithm can analyze the levels in conjunction with respective reference value ranges for the one or more biomarkers. The algorithm can perform, for example, linear regression analysis on the levels of each of one or more biomarkers.

According to various embodiments, a method for screening a subject to identify the presence or absence of NASH in the subject can comprise measuring the level of a plurality of biomarkers in a sample derived from the subject, wherein the plurality of biomarkers comprises an adipocytokine, an apoptosis marker, and a cell death marker, and analyzing the levels in conjunction with respective reference value ranges for the plurality of biomarkers. Based on this analysis, the presence or absence of NASH in the subject can be determined. The reference value ranges of each of the plurality of biomarkers can represent, for example, a subject without NASH. According to various embodiments, the analysis can comprise multivariate analysis, for example, linear regression analysis, of the level of one or more biomarkers. The analysis can calculate, for example, an optimal threshold for detecting NASH. The threshold can be calculated, for example, at a value greater than or equal to about 0.20, a value in a range of from about 0.20 to about 0.70, from about 0.25 to about 0.55, or from about 0.27 to about 0.40. According to various embodiments, a threshold value can be selected to provide a sensitivity for detecting NASH in a range of, for example, from about 50% to about 100%, and a specificity for detecting NASH in a range of, for example, from about 25% to about 90%.

As disclosed herein in Example 2, a panel of one or more biomarkers performed well in identifying the presence or absence of NASH in a subject. In particular, a panel (NASH Diagnostics panel) of cytokeratin CK-18 (M65 antigen), caspase-cleaved CK-18 (M30-antigen), resistin, and adiponectin was capable of identifying the presence or absence of NASH in a subject with a sensitivity of greater than 95%, and a specificity of greater than 70% (See, Table 3). As further shown in Table 3, when the threshold cut-off is 0.2075, the NASH Diagnostics panel can identify the presence or absence of NASH in a subject with a sensitivity of 100%, and a specificity of 46.8%.

According to various embodiments, one model for predicting a diagnosis of NASH comprises a combination of caspase-cleaved CK-18 (M30 antigen), intact CK-18 (M65 antigen), adiponectin, and resistin measurements. Using this model, at a threshold value of 0.2085, nineteen (19) out of twenty-four (24) patients with NAFLD (79.2%) could avoid a liver biopsy. The use of this biomarker set could lead to significant decrease in the liver biopsies needed to establish a diagnosis of NAFLD, for example, a diagnosis of NASH. Utilizing a lower threshold value (e.g., 0.2085) versus a higher threshold value (e.g., 0.550) can produce a lower positive predictive value (70.4% versus 84.6%), and some subjects diagnosed as NASH by this model may not necessarily have NASH. Nevertheless, these subjects will not be harmed by a false positive diagnosis, given that the management of NASH mostly relies on exercise and weight loss approaches generally beneficial for the subjects' well-being and health.

According to various embodiments, the method can further comprise a step of utilizing the level of one or more biomarkers of the plurality of biomarkers as an auxiliary marker, for example, in combination with using HOMA score, for identifying the presence or absence of NASH.

According to various embodiments, a method for evaluating the effect of an agent for treating NASH in a subject can comprise analyzing the level of each of one or more biomarkers in samples derived from the subject before and after the subject is treated with the agent, in conjunction with respective reference value ranges for the one or more biomarkers, wherein the one or more biomarkers comprises an adipocytokine, an apoptosis marker, a cell death marker, or any combination thereof.

The terms "treat" or "treating" as used herein, means management or care of a subject for the purpose of combating, alleviating, reducing, relieving, improving, eliminating, etc., one or more signs or symptoms associated with NASH. The term "agent" as used herein, refers to a chemical compound, a mixture of chemical compounds, a biological macromolecule, or an extract made from biological materials. The term "agent for treating" as used herein, refers to an agent capable of inducing a desired therapeutic effect when properly administered to a subject.

As described herein, the "level" of a biomarker can be a relative or absolute amount and can be a direct or indirect measurement of the biomarker. In addition, the value of the level can be obtained from a secondary source, such as a physician or diagnostic laboratory or can be determined using any convenient sample and assay, including but not limited to those described herein.

According to various embodiments, a method for monitoring the efficacy of a therapy for treating NASH in a subject can comprise analyzing the level of each of one or more biomarkers in samples derived from the subject before and after the subject undergoes the therapy, in conjunction with respective reference value ranges for the one or more biomarkers, wherein the one or more biomarkers comprises an adipocytokine, an apoptosis marker, a cell death marker, or any combination thereof.

The term "therapy" as used herein, encompasses the treatment of existing NASH as well as preventative treatment (i.e., prophylaxis). Therapy includes, but is not limited to, administering an agent for treating NASH, treating associated metabolic conditions such as diabetes and hyperlipidemia, improving insulin resistance, following a balanced and healthy diet, avoiding alcohol, and avoiding unnecessary medications.

According to one or more further embodiments of the present teachings, kits for use in the methods of the teaching are provided. In some embodiments, the kit can comprise a package containing one or more agent for measuring the level of an analyte of interest, wherein the analyte of interest comprises at least one of cytokeratin CK-18 (M-65-antigen), caspase-cleaved CK-18 (M30-antigen), resistin, adiponectin, or any combination thereof. The one or more agent can comprise, for example, an antibody of cytokeratin CK-18 (M-65 antigen), an antibody of caspase-cleaved CK-18 (M30-antigen), an antibody of resistin, an antibody of adiponectin, or any combination thereof. The kit can further comprise at least four separate containers inside the package, wherein each separate container contains a respective one or more of the antibodies. The kit can further comprise one or more control reference samples.

According to various embodiments, the package can comprise a box, and a wrapper enveloping the box. The package can be hermetically sealed. The package can be wrapped in shrink wrap. The kit can further comprise instructions for using the kit.

According to various embodiments, the kit can further comprise information in electronic or paper form. The information can comprise, for example, instructions for measuring the level of the analyte of interest. The information can also comprise, for example, reference levels for comparing to detected levels of each of the analytes of interest, and/or instructions to correlate the detected levels of each of the analytes of interest with NAFLD.

The following examples are illustrative only, and are not intended to limit the present teachings.

Example 1

Patient Population

Serum samples were obtained from the Epidemiology of Nonalcoholic Fatty Liver Disease (EPI-NAFLD) database and specimen repository at Inova Fairfax Hospital, Falls Church, Va. The EPI-NAFLD database-specimen repository was created by enrolling consecutive patients undergoing bariatric surgery at Inova Fairfax Hospital. The EPI-NAFLD database contains the extensive clinical and laboratory data routinely collected for each bariatric surgery patient after obtaining informed consent. Patients with evidence of excessive alcohol use (greater than or equal to 10 grams/day) or other causes of liver disease were excluded from this analysis. In addition to extensive clinical and laboratory data, each patient included in this study had a liver biopsy at the time of surgery. Each liver biopsy was read by a single pathologist (ZG) using standardized pathologic approach.

This study included a total of 101 patients. Of these, 69 patients were part of the "Biomarker Development Set" and 32 were part of the "Biomarker Validation Set." The Biomarker Development Set included three groups of patients: (1) biopsy-proven NASH (NASH, N=22); (2) biopsy-proven Simple Steatosis (SS, N=15); and (3) age- and BMI-matched Controls whose liver biopsy did not show NAFLD (Controls, N=32). Additionally, the Biomarker Validation Set included patients with biopsy-proven NASH or biopsy-proven Simple Steatosis (N=32) who were randomly selected from the same database. Histology and the clinical characteristics of the Validation Set were blinded for all the investigators performing the validation assays and subsequent analysis. After the completion of biomarker validation, the characteristics of the validation set were unblinded. Of these patients (N=32), 21 had histological NASH and 11 had histological Simple Steatosis.

Other liver diseases were excluded for all patients (e.g., hepatitis B, hepatitis C, autoimmune liver disease). Patients with excessive alcohol use (greater than 10 gram/day) and those receiving treatment with PPAR-γ agonists were also excluded. Fasting serum specimens were obtained at the time of biopsy and stored at −80 C.

Histopathology

Each liver biopsy specimen was fixed in formalin, routinely processed for histology, sectioned, and stained with hematoxylin-eosin and Masson trichrome. All biopsies were evaluated by a single hepatopathologist (ZG). The degree of steatosis was assessed in hematoxylin-eosin-stained sections and graded as an estimate of the percentage of tissue occupied by fat vacuoles as follows: 0=none; 1=<5 percent; 2=6-33 percent; 3=34-66 percent; 4=>66 percent. Other histological features evaluated in hematoxylin-eosin sections included portal inflammation, lymphoplasmacytic lobular inflammation, polymorphonuclear lobular inflammation, Kupffer cell hypertrophy, apoptotic bodies, focal parenchymal necrosis, glycogen nuclei, hepatocellular ballooning, and Mallory bodies.

These histological features were graded as follows: 0=none; 1=mild or few; 2=moderate; and 3=marked or many. Fibrosis was assessed with the Masson trichrome stain. Portal fibrosis and interlobular pericellular fibrosis were graded as follows: 0=none; 1=mild; 2=moderate; and 3=marked. When present, bridging fibrosis was noted as few or many bridges, and cirrhosis was identified by parenchymal nodules surrounded by fibrous tissue. Cirrhosis was further categorized as incomplete or established, depending on the degree of loss of acinar architecture. Each liver biopsy was assigned to one of four diagnostic categories: (1) no fatty liver disease present (Obese Controls); (2) simple steatosis (SS); (3) steatosis with nonspecific inflammation (excluded); or (4) NASH. Patients were defined as having simple steatosis if they had any degree of hepatocellular fat accumulation as their sole pathology. Patients with steatosis and nonspecific inflammation had, in addition to fat, spotty hepatocellular dropout with focal inflammation or Kupffer cell hypertrophy. These patients were excluded from this analysis. NASH was identified when in addition to steatosis, there was one or more of the following pathologic features: (1) prominent hepatocellular ballooning with associated lobular inflammation; (2) Mallory bodies; (3) perisinusoidal fibrosis in a perivenular location.

The Homeostasis Model Assessment (HOMA)

Glucose levels were measured by Glucose Oxidase-based kits (Sigma-Aldrich, St. Louis, Mo., USA) according to the manufacturer's protocol. Insulin levels in serum samples were quantified by sandwich ELISA (LINCO Research, St. Charles, Mo., USA). HOMA scores were obtained with HOMA Calculator software, version 2.2 (Oxford Centre for Diabetes, Endocrinology, and Metabolism, Oxford, UK). The analyses were subdivided in three groups of patients: High HOMA (>3.0); Low HOMA (<1.8); and Mid-range HOMA (1.8-3.0).

Measurements of Adipocytokines and Cytokines

Serum levels of adipocytokines and cytokines were measured with enzyme immunoassays according to the manufacturers' instructions. Each measurement was performed in duplicate. TNF-α, IL-6, and IL-8 were measured using Compact ELISA kits from RDI Division of Fitzgerald Industries International (Concord, Mass., USA). Resistin levels were assessed with kits provided by BioVendor Laboratory Medicine, Inc. (Candler, N.C., USA). Adiponectin and visfatin levels were measured with competitive ELISA assays from Phoenix Pharmaceuticals, Inc. (Belmont, Calif., USA). The absorbance values were measured with an ELISA Reader at 450 nanometers (nm). Calibration curves were constructed by plotting the net average absorbance of the standards on the Y-axis, the concentrations of the standards on the X-axis, and using logit-log function to linearize and draw the best fitting curve. Concentrations of the adipocytokines in each sample were calculated from the calibration curve with Sigma Plot software v.7 (Systant Software, Inc., San Jose, Calif.). The correlation coefficients were linear in a concentration range from 1 pg/ml to 700 pg/ml for TNF-α (r=0.973); from 2 pg/ml to 300 pg/ml for IL-8 (r=0.989); from 1.5 pg/ml to 400 pg/ml for IL-6 (r=0.968); from 1.82 ng/ml to 49 ng/ml for visfatin (r=0.977); from 1.5 ng/ml to 50 ng/ml for resistin (r=0.969); from 0.3 µg/ml to 100 µg/ml for adiponectin (r=0.975); and from 2 µU/ml to 200 µU/ml for insulin (r=0.982). The samples with higher concentrations of analytes were quantified after appropriate dilutions.

Measurements of Apoptosis and Necrosis

Cytokeratin CK-18 (M65 antigen) and caspase-cleaved CK-18 (M30 antigen) were measured using M65 and M30 Apoptosense™ ELISA Kits (AXXORA, LLC, San Diego, Calif.), respectively. Each measurement was performed in duplicate. Concentrations of the antigens in each sample were calculated from a calibration curve as described above.

were used to test for significant relations in continuous data with adjustment for possible confounders. Unless otherwise noted, 2-tailed hypothesis tests and p-values<0.05 were considered significant.

Results

Clinical, demographic, and adipocytokine data for the Biomarker Development Set are summarized in Table 1. The three groups (SS, NASH, and Controls) were well-matched in terms of age, gender, ethnic background, and measures of obesity (BMI and Hip/Waist ratio). Additionally, fasting serum insulin (8.9±6.4, 10.7±6.7, and 10.3±15.0, respectively) and HOMA score (2.1±2.2, 3.4±2.3, and 3.2±7.0, respectively) were similar between the three groups. Patients with NASH had higher aspertate transaminase (AST), and alanine transaminase (ALT) levels, higher fasting glucose levels, and higher IL-6 levels, but lower adiponectin and visfatin levels. Serum TNF-α, IL-8 and resistin levels were not significantly different between NASH and SS.

TABLE 1

Clinical, demographic, and laboratory data of training and validation patient cohorts (mean ± SD or %). Validation dataset was comprised of 29.1% of Simple Steatosis patients and 70.9% of NASH patients. Liver histology was available for all patients including those from the Control group.

| Clinical parameter | Simple Steatosis (training) (N = 15) | NASH (training) (N = 22) | Matched Controls (training) (N = 32) | Validation Set (N = 32) |
|---|---|---|---|---|
| Age, years | 37.4 ± 8.3 | 42.5 ± 10.4 | 39.3 ± 9.8 | 41.6 ± 10.6 |
| Female, % | 93.3% (14) | 59.1% (13) | 90.6% (19) | 70.9% |
| Caucasian, % | 73.3% (11) | 72.7% (16) | 78.% (25) | 75% |
| Hip-to waist ratio | 1.06 ± 0.11 | 1.01 ± 0.1 | 1.07 ± 0.13 | 1.07 ± 0.13 |
| Body mass index | 45.7 ± 4.8 | 48.2 ± 8.7 | 47.0 ± 9.1 | 52.30 ± 13.08 |
| AST level, IU/L (*) | 19.9 ± 6.8 | 35.9 ± 27.1 | 18.0 ± 3.7 | 32.9 ± 30.3 |
| ALT level, IU/L (*) | 22.1 ± 12.2 | 47.9 ± 32.1 | 21.9 ± 8.1 | 42.4 ± 34.3 |
| Serum triglyceride, mg/dL | 154.6 ± 88.8 | 177.8 ± 78.3 | 134.9 ± 73.4 | 177.1 ± 87.6 |
| Serum cholesterol, mg/dL | 192.2 ± 42.7 | 193.4 ± 32.7 | 178.6 ± 27.9 | 205.7 ± 29.6 |
| Serum glucose, mg/dL (*) | 109.6 ± 24.1 | 128.45 ± 46.5 | 103.6 ± 24.4 | 102.8 ± 16.9 |
| TNF-α, pg/ml | 2.8 ± 0.9 | 9.1 ± 23.6 | 1.9 ± 0.2 | NA |
| IL-8, pg/ml | 26.9 ± 56.5 | 24.0 ± 29.4 | 7.3 ± 3.1 | NA |
| IL-6, pg/ml (*) | 51.1 ± 122.5 | 8.0 ± 2.9 | 7.2 ± 5.3 | NA |
| Resistin, ng/ml | 7.9 ± 3.4 | 5.9 ± 3.0 | 7.9 ± 4.1 | 5.43 ± 3.27 |
| Adiponectin, µg/ml (*) | 12.1 ± 8.4 | 6.1 ± 5.2 | 9.3 ± 6.3 | 9.48 ± 4.48 |
| Visfatin, pg/ml (*) | 52.5 ± 67.0 | 16.7 ± 6.3 | 25.8 ± 18.0 | NA |

(*) P-values: Fasting serum glucose (p < 0.03); AST (p < 0.0011); ALT (p < 0.0001); IL-6 (p < 0.04); adiponectin (p < 0.03); visfatin (p < 0.008)

Statistical Analyses

Variables are presented as Mean+/−Standard Deviation (SD), or as percentages. Between groups of patients, pairwise comparisons of the serum concentrations of insulin, glucose, visfatin, TNF-α, resistin, adiponectin, IL-8, IL-6, as well as M30 and M65 antigens, were performed by non-parametric Mann-Whitney tests. One-way ANOVA test or the Kruskal-Wallis test was used to compare three or more groups. Linear regression analysis was performed with S-PLUS v. 7.0 (Insightful Corporation, Seattle, Wash., USA). The sensitivity, specificity, positive predictive values, negative predictive values and confidence intervals (CI) were assessed using MedCalc Receiver Operating Characteristic (ROC) curve analysis software (MedCalc, Mariakerke, Belgium).

Associations between the concentration levels for pairs of adipocytokines and cytokines of interest were tested with the use of Pearson correlation coefficients after appropriate log-normalizations of concentration values. Additionally, multivariate linear regressions with stepwise variable selection Cytokeratin CK-18 and Caspase-Cleaved CK-18 Levels in NAFLD Three interdependent surrogate end-points were assessed to determine the relative levels of apoptosis and necrosis in NAFLD: (1) the total level of caspase-cleaved CK-18 (M30 antigen, released in the process of caspase cleavage and reflecting on apoptosis); (2) the total released amount of cytokeratin CK-18 (M65 antigen, released from all dying cells and reflecting on total cell death including both apoptosis and necrosis); and (3) necrosis-reflecting parameter calculated as M65 minus M30 (M65−M30).

Referring to FIG. 1 a scatter plot showing the results of ELISA analysis of caspase-cleaved CK-18 (M30 antigen) of serum samples derived from NASH patients, SS patients, and BMI-matched Normal Control patients is shown. In the scatter plot, each dot represents one subject, and dashed lines represent the mean value for each group. Patients with NASH had significantly higher levels of M30 antigen (p<0.02) than subjects with SS, and Control subjects (NASH 307.0+/−278.2 IU/L; SS 127.3+/−62.2 IU/L; Controls 137.4+/−36.8

IU/L). Differences in concentrations of M30 antigen between patients with SS and Controls did not reach statistical significance.

The levels of apoptosis in NAFLD patients were positively correlated with HOMA scores (R=0.5106, p=0.0013). The differences in the levels of apoptosis were highly significant (p<0.001) when NAFLD patients were subdivided according to their HOMA scores (High HOMA scores, N=15 vs. Mid- and Low-HOMA scores, N=22).

Quantification of the M65 antigen (intact CK-18) that served as a measure of total cell death followed the same trend as M30 antigen (cleaved CK-18) measurements, with significantly higher antigen levels in NASH vs. SS (p<0.003). In NAFLD patients, the correlation of overall cell death and HOMA scores remained significant (R=0.51, p<0.002). When NAFLD patients were subdivided according to their HOMA scores as described above, the differences in the levels of total cell death remained significant (p<0.0002).

One parameter closely reflecting necrotic cell death is calculated as M65−M30. Patients with SS differed from those with NASH (p<0.05), but not from the Controls. The correlation between necrosis and HOMA scores was not significant. Subdividing the NASH patients according to their necrosis levels discriminated between patients with High-HOMA and Mid- and Low-HOMA scores (p<0.001).

Relationship Between Levels of CK-18 Antigens and Adipocytokines in NAFLD Patients In the entire cohort (NAFLD and Controls), markers of apoptosis (as measured by levels of caspase-cleaved CK-18) correlated with TNF-α levels and IL-8 levels (R=0.4986, p≦1.395e-05 and R=0.3052, p≦0.0108, respectively). On the other hand, in the NAFLD cohort (NASH and SS), caspase-cleaved CK-18 levels only correlated with TNF-α (R=0.4816, p≦0.002626). Similarly, in the entire cohort, measurements of total cell death positively correlated with both TNF-α levels and IL-8 levels (R=0.3277, p≦0.006007, and R=0.3095, p≦0.009697, respectively). However, in the NAFLD cohort, this correlation, although relatively weak, remained significant only for TNF-α (R=0.3049, p≦0.06669). There were no significant correlations in the levels of CK-18 derived antigens with any other adipocytokine profiled.

Models Predicting Histologic NASH

Additional analyses revealed that the levels of M30 antigen (cleaved CK-18) predicted histological NASH with 70% sensitivity and 83.7% specificity (AUC=0.711, p<10−4), whereas the predictive value of the levels of M65 antigen (intact CK-18) was somewhat higher, 63.6% sensitivity and 89.4% specificity (AUC=0.814, p<10$^{-4}$).

On the other hand, multivariate analysis revealed that histological NASH could be predicted by a combination of cleaved CK-18 (M30 antigen, apoptosis), a product of the subtraction of cleaved CK-18 level from intact CK-18 level (M65−M30, necrosis), serum adiponectin and serum resistin. This combination set had a sensitivity of 95.45%, and a specificity of 70.21%, (AUC=0.908, p<10−4), as detailed in Table 2.

TABLE 2

Best fitting multiple linear regression model distinguishes NASH patients within the cohort of NAFLD and non-NAFLD controls. Regression coefficient β represents slope estimate ± Standard Error of the estimate (SE).

| Model | Independent variable | Regression coefficient β and SE | P-values of independent variables | P-value of the whole model |
|---|---|---|---|---|
| Prediction of histologic NASH | (Intercept) | 0.4909 +/− 0.1351 | <0.0006 | P < 1.232e$^{-6}$ |
| | M30, IU/L | 0.0011 +/− 0.0003 | <0.0001 | |
| | M65-M30, IU/L | 0.0003 +/− 0.0001 | <0.0548 | |
| | Adiponectin, μg/ml | −0.0153 +/− 0.0069 | <0.0316 | |
| | Resistin, ng/ml | −0.0418 +/− 0.0125 | <0.0014 | |

Performance-related characteristics of the models of predicting NASH are summarized in the Table 3.

TABLE 3

Performance of models predicting NASH.

| Model | Cut-off | Sensitivity % (95% CI) | Specificity % (95% CI) | PPV % | NPV % | Negative likelihood ratio | AUC (95% CI) | Model p-value |
|---|---|---|---|---|---|---|---|---|
| Full model (Multi-variate) | 0.2772 | 95.45 (77.1-99.2) | 70.21 (55.1-82.6) | 60.0 | 97.1 | 0.065 | 0.908 | <10$^{-5}$ |
| | 0.3499 | 77.27 (54.6-92.1) | 87.23 (74.2-95.1) | 73.9 | 89.1 | 0.26 | (0.814-0.964) | |
| | 0.2075 | 100.00 (84.4-100.0) | 46.81 (32.1-61.9) | 46.8 | 100.0 | 0.00 | | |
| M30, U/L | 174.1 | 63.64 (40.7-82.8) | 87.23 (74.2-95.1) | 70.0 | 83.7 | 0.42 | 0.711 | <10$^{-4}$ |
| | 111.6 | 81.82 (59.7-94.7) | 29.79 (17.4-44.9) | 35.3 | 77.8 | 0.61 | (0.589-0.814) | |
| | 261.35 | 36.36 (17.2-59.3) | 97.87 (88.7-99.6) | 88.9 | 76.7 | 0.65 | | |

TABLE 3-continued

Performance of models predicting NASH.

| Model | Cut-off | Sensitivity % (95% CI) | Specificity % (95% CI) | PPV % | NPV % | Negative likelihood ratio | AUC (95% CI) | Model p-value |
|---|---|---|---|---|---|---|---|---|
| M65, U/L | 384.3 | 63.64 (40.7-82.8) | 89.36 (76.9-96.4) | 73.7 | 84.0 | 0.41 | 0.814 (0.702-0.897) | $<10^{-4}$ |
| | 242.9 | 86.36 (65.1-96.9) | 65.96 (50.7-79.1) | 54.3 | 91.2 | 0.21 | | |
| | 545 | 36.36 (17.2-59.3) | 95.74 (85.4-99.4) | 80.0 | 76.3 | 0.66 | | |

Positive predictive value: PPV,
Negative predictive value: NPV,
95% Confidence Interval: CI.
Cut-off values correspond to the highest accuracy value (minimal false positive and false negative results).

Example 2

Validation in Predicting Histological NASH

To validate the model described here, a blinded cohort of NAFLD patients (N=32) was subjected to the same measurement. The histological findings NAFLD as well as the clinical and the biochemical variables were blinded until completion of the analysis. After the analysis was complete, clinical and demographic data for the "Biomarker Validation Set" were un-blinded. As depicted in Table 1, no differences were observed between the two sets of patients.

The performance of the NASH Diagnostics model in the validation was characterized by an AUC of 0.732 with a 95% confident interval (CI) of 0.55-0.87. A threshold of 0.3825 for the model was associated with a sensitivity of 71.4%, a specificity of 72.7%, a positive predictive value of 83.3% %, and a negative predictive value of 57.1%. A full list of thresholds for the validation set is depicted in Table 4. As noted in Table 4, the model had the best Positive Predictive Value (PPV) when a threshold of 0.5500 was chosen. The best Negative Predictive Value (NPV) for the model was obtained at a threshold of 0.2085.

TABLE 4

Results of the blinded validation of NASH Diagnostics model predicting of NASH.

| Threshold | TP | FP | TN | FN | Sensitivity % | Specificity % | PPV % | NPV % |
|---|---|---|---|---|---|---|---|---|
| 0.2085 | 19 | 8 | 3 | 2 | 90.5 | 27.3 | 70.4 | 60.0 |
| 0.2793 | 19 | 8 | 3 | 2 | 90.5 | 27.3 | 70.4 | 60.0 |
| 0.2805 | 19 | 8 | 3 | 2 | 90.5 | 27.3 | 70.4 | 60.0 |
| 0.3199 | 17 | 6 | 5 | 4 | 81.0 | 45.5 | 73.9 | 55.6 |
| 0.3377 | 16 | 5 | 6 | 5 | 76.2 | 54.5 | 76.2 | 54.5 |
| 0.3692 | 15 | 4 | 7 | 5 | 75.0 | 63.6 | 78.9 | 58.3 |
| 0.3825 | 15 | 3 | 8 | 6 | 71.4 | 72.7 | 83.3 | 57.1 |
| 0.5500 | 11 | 2 | 9 | 10 | 52.4 | 81.8 | 84.6 | 47.7 |

Positive predictive value: PPV,
Negative predictive value: NPV,
True Positives: TP,
True Negatives: TN,
False Positives: FP,
False Negatives: FN.

The NASH diagnostics model predicted the diagnosis of NASH utilizing the following formula: NASH=0.49087199+ 0.00113565×M30(IU/L)+0.00027678×(M65−M30)(IU/L)− 0.01525278×Adiponectin (μg/ml)−0.04181620×Resistin (ng/ml). Calculated NASH values falling above the chosen threshold value indicate a diagnosis of NASH.

In order to further assess the performance of this model, the training dataset was extended to all 101 patients by inclusion of the subjects whose clinical data were uncovered after the completion of the validation phase. This extension resulted in a model with an increase of the optimal threshold to 0.4320 (AUC of 0.854, 95% CI of 0.770 to 0.917, p<2.1e$^{-7}$), which associated with a sensitivity of 72.1%, and specificity of 91.4%.

The extended NASH diagnostics model predicted the diagnosis of NASH utilizing the following formula: NASH=0.47674544+0.00098349×M30(IU/L)+ 0.00021301×(M65−M30)(IU/L)−0.01523809×Adiponectin (μg/ml)−0.02697178×Resistin (ng/ml).

It is clear that the methods of the present teachings can be practiced, if desired, by measuring the level of one or more biomarkers in a sample derived from the subject, wherein the one or more biomarkers comprises an adipocytokine, an apoptosis marker, a cell death marker, or any combination thereof, and detecting the presence or absence of an abnormal level of the one or more biomarkers, without assaying for any additional markers or evaluating any other clinical characteristics. In addition, the one or more biomarkers can be used in combination with one or more additional biomarkers, or in combination with the evaluation of one or more clinical variable.

In one or more embodiments, the teachings provides a method for detecting the presence or severity of NAFLD in a subject by measuring the level of an adipocytokine, an apoptosis marker, a cell death marker, or any combination thereof, in a sample, and also measuring the level of at least one additional biomarker. Additional biomarkers, include, for example, sterols, bile acids, eicosanoids, chemokines, cytokines, and cytokeratins.

In one or more embodiments, a method for detecting the presence or severity of NAFLD in a subject comprises measuring the level of an adipocytokine, an apoptosis marker, a cell death marker, or any combination thereof, in a sample, and evaluating one or more clinical variable, such as patient age or gender, body mass index (obesity), glucose metabolism, insulin resistance, diabetes, hyperlipidemia, and/or echographic variables. It is understood that the analysis of these and other well known clinical or echographic variables can be useful in a method of the teachings. Furthermore, a method of the teachings encompasses determination of the clinical or echographic variable, or can rely on one or more historic, or previously determined clinical or echographic variables.

Those skilled in the art can appreciate from the foregoing description that the present teachings can be implemented in a variety of forms. Therefore, while these teachings have been described in connection with particular embodiments and examples thereof, the present teachings should not be so limited. Various changes and modifications can be made without departing from the scope of the present teachings.

What is claimed is:

1. A method for detecting non-alcoholic fatty liver disease (NAFLD) in a subject, the method comprising:
    measuring the level of one or more biomarkers in a sample derived from the subject, wherein the one or more biomarkers comprises an adipocytokine, an apoptosis marker, a cell death marker, or any combination thereof; and
    analyzing the level in conjunction with a respective reference value range for said one or more biomarkers.

2. The method of claim 1, wherein analyzing the level in conjunction with a respective reference value range comprises performing linear regression analysis with stepwise variable selection.

3. The method of claim 1, wherein the NAFLD is simple steatosis, steatosis with non-specific inflammation, non-alcoholic steatohepatitis (NASH), or NASH-related cirrhosis.

4. The method of claim 1, wherein the one or more biomarkers comprises at least two biomarkers and two or more of the biomarkers are measured.

5. The method of claim 1, wherein the one or more biomarkers comprises cytokeratin CK-18 (M65 antigen), caspase-cleaved CK-18 (M30-antigen), resistin, adiponectin, visfatin, glucose, insulin, tumor necrosis factor-alpha (TNF-α), interleukin 6 (IL-6), or interleukin 8 (IL-8), or any combination thereof.

6. The method of claim 1, wherein the one or more biomarkers is cytokeratin CK-18 (M65 antigen), caspase-cleaved CK-18 (M30-antigen), resistin, or adiponectin, or any combination thereof.

7. The method of claim 1, wherein the one or more biomarkers is cytokeratin CK-18 (M65 antigen), TNF-α, resistin, or adiponectin, or any combination thereof.

8. The method of claim 1, further comprising measuring a level of necrosis by subtracting the level of apoptosis marker from the level of cell death marker.

9. The method of claim 1, wherein the subject is a human being.

10. The method of claim 1, wherein said measuring comprises reacting with a specific antibody against the one or more biomarkers, or any fragment thereof containing an antigenic determinant.

11. The method of claim 10, wherein the specific antibody comprises a whole immunoglobulin molecule, a monoclonal antibody, a polyclonal antibody, a chimeric antibody, a recombinant fragment of antibody, an Fab fragment, an Fab' fragment, an F(ab')2 fragment, an Fv fragment, or an scFv fragment, or any combination thereof.

12. The method of claim 1, wherein said measuring the level of one or more biomarkers comprises conducting enzyme-linked immunosorbent assay (ELISA), radioimmunoassay (RIA), immunofluorescent assay (IFA), sandwich assay, magnetic capture, microsphere capture, Western Blot, surface enhanced Raman spectroscopy (SERS), flow cytometry, or mass spectrometry.

13. The method of claim 1, wherein the sample comprises blood, serum, plasma, urine, saliva, cerebrospinal fluid, tissue, or tissue extract.

14. The method of claim 1, wherein said measuring comprises an adipocytokine, and apoptosis marker, a cell death marker, or any combination thereof, in a multiplex assay.

15. The method of claim 1, the method further comprising:
    generating data on the sample indicating the level of the one or more biomarkers;
    transforming the data into computer readable form;
    operating a computer to execute an algorithm, wherein the algorithm determines the level of said one or more biomarkers; and
    displaying the level.

16. A method for screening a subject to identify the presence or absence of non-alcoholic steatohepatitis (NASH) in the subject, the method comprising:
    measuring the level of a plurality of biomarkers in a sample derived from the subject, wherein the plurality of biomarkers comprises an adipocytokine, an apoptosis marker, and a cell death marker; and
    analyzing the levels in conjunction with respective reference value ranges for said plurality of biomarkers.

17. The method of claim 16, wherein analyzing the levels in conjunction with respective reference value ranges comprises performing linear regression analysis.

18. The method of claim 16, further comprising utilizing Homeostasis Model Assessment (HOMA) to identify the presence or absence of NASH.

19. The method of claim 16, wherein the reference value ranges of each of the plurality of biomarkers represent a subject without NASH.

20. A method for evaluating the effect of an agent for treating non-alcoholic steatohepatitis (NASH) in a subject, the method comprising:
    analyzing the level of each of one or more biomarkers in samples derived from the subject before and after the subject is treated with said agent, in conjunction with respective reference value ranges for said one or more biomarkers, wherein the one or more biomarkers comprises an adipocytokine, an apoptosis marker, a cell death marker, or any combination thereof.

21. A method for monitoring the efficacy of a therapy for treating non-alcoholic steatohepatitis (NASH) in a subject, the method comprising:
    analyzing the level of each of one or more biomarkers in samples derived from the subject before and after the subject undergoes said therapy, in conjunction with respective reference value ranges for said one or more biomarkers, wherein the one or more biomarkers comprises an adipocytokine, an apoptosis marker, a cell death marker, or any combination thereof.

22. A kit comprising a package, the package containing at least four agents, for measuring the level of at least four analytes of interest, wherein the at least four analytes of interest comprise cytokeratin CK-18 (M65 antigen), caspase-cleaved CK-18 (M30-antigen), resistin, and adiponectin.

23. The kit of claim 22, wherein the at least four agents comprise at least one of an antibody of cytokeratin CK-18 (M65 antigen), an antibody of caspase-cleaved CK-18 (M30-antigen), an antibody of resistin, an antibody of adiponectin, and a combination thereof.

24. The kit of claim 22, further comprising at least four separate containers inside the package, wherein each separate container contains a respective one of the at least four agents.

25. The kit of claim 22, further comprising one or more control reference sample.

26. The kit of claim 22, wherein the package comprises a box, a wrapper enveloping the box, and instructions for using the kit.

27. The kit of claim 22, further comprising information, in electronic or paper form, comprising reference levels for comparing to detected levels of each of the at least four analytes of interest.

28. The kit of claim 22, further comprising information, in electronic or paper form, comprising instructions to correlate the detected levels of each of the at least four analytes of interest with non-alcoholic fatty liver disease (NAFLD).

* * * * *